United States Patent [19]

Kurtz et al.

[11] 4,405,309
[45] Sep. 20, 1983

[54] SURGICAL DRAINAGE DEVICE WITH METERED AIR PUMP

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 256,152

[22] Filed: Apr. 21, 1981

[51] Int. Cl.³ ............................................. A61M 1/00
[52] U.S. Cl. ..................................... 604/317; 604/321
[58] Field of Search ...................... 128/276–278; 141/7, 59; 417/511, 513, 249, 426; 604/48, 73, 317, 320, 321, 319; 137/205

[56] References Cited

U.S. PATENT DOCUMENTS 3,187,960  6/1965  Gorman ............................. 417/511
3,750,692  8/1973  Tibbs ..................................... 141/59
4,312,351  1/1982  Kurtz et al. ........................ 128/276

FOREIGN PATENT DOCUMENTS 971034   7/1975  Canada ............................. 417/511
856216  12/1960  United Kingdom ............. 417/249
602186   4/1978  U.S.S.R. ............................ 128/276

Primary Examiner—Richard J. Apley
Assistant Examiner—J. L. Kruter
Attorney, Agent, or Firm—Larson and Taylor

[57] ABSTRACT

A surgical underwater drainage device is provided for draining fluids from the body of a patient through an inlet tube. A metered air pump is fluidly connected to the inlet tube so as to deliver a metered amount of air to the inlet tube when excess negativity occurs there. A spring biased closed one-way valve in the metered air pump prevents atmospheric air from entering the inlet tube except during actuation of the metered air pump.

12 Claims, 5 Drawing Figures

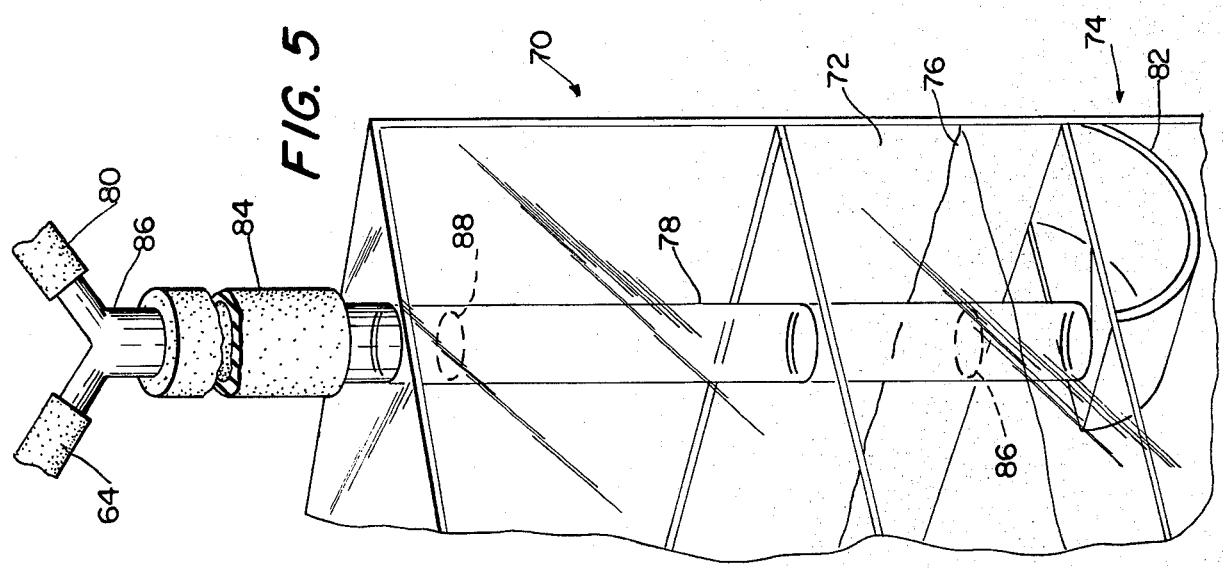
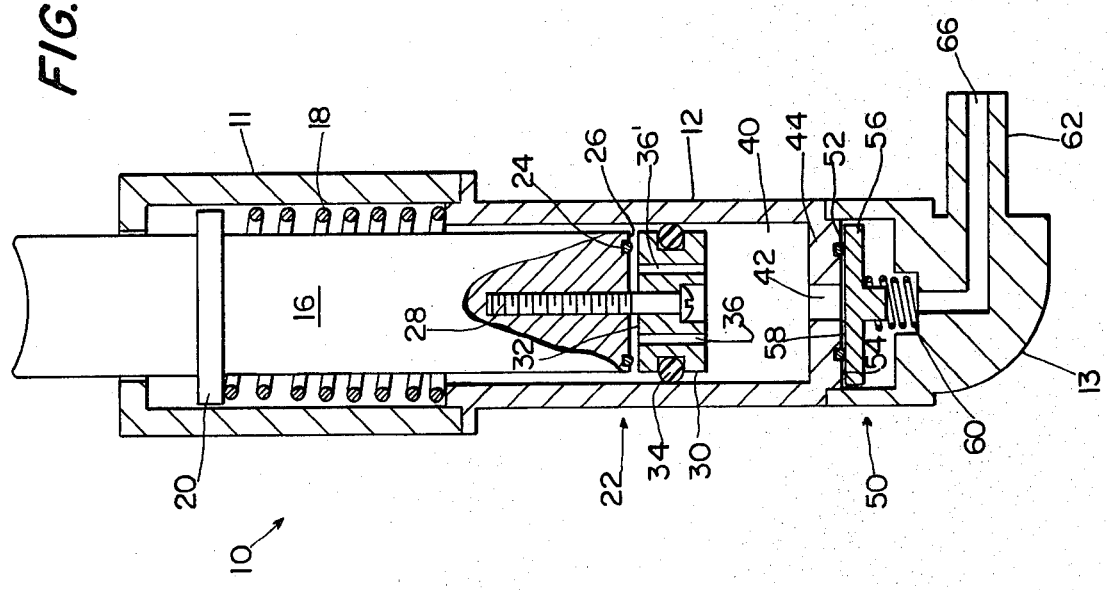

SURGICAL DRAINAGE DEVICE WITH METERED AIR PUMP

FIELD OF THE INVENTION

This invention relates to a surgical underwater drainage system used in draining fluids from the body, e.g. the pleural cavity, and is particularly concerned with an improved drainage system which relieves excess negativity within the body cavity.

BACKGROUND OF THE INVENTION

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the rib cage or such as occur, for example, where the patient has pleurisy, generates fluids in the pleural cavity which tend to obstruct normal breathing. It is necessary to provide a device which can remove these fluids from the pleural cavity and at the same time ensure that the desired degree of negative pressure is maintained within the pleural cavity.

One of the basic types of apparatus which have been used for this purpose is shown, for example, in U.S. Pat. Nos. 3,363,626 and 3,363,627. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity. However, such an apparatus required prefilling the underwater seal chamber with water and also prefilling the pressure manometer chamber to the desired level to maintain the desired degree of negativity within the pleural cavity.

In order to avoid the necessity and problems of having to prefill chambers in a drainage device, the underwater seal chamber is located at the lower end of the thorocotomy tube. In this manner, the underwater seal is formed by liquid drained from the patient's pleural cavity. Drainage systems of this nature are disclosed in U.S. Pat. No. 4,015,603 and applicants pending U.S. application Ser. Nos. 107,329 and 120,295.

It has been found that doctors frequenty will "milk" the thoracotomy tubes in an effort to remove any clots or obstructions from the tube. This milking of the tube is achieved by squeezing the flexible thoracotomy tube adjacent the upper end and drawing the fingers down the tube to cause the fluids within the tube to be passed out the lower end of the tube. Obviously, this action has the effect of substantially increasing the degree of nagativity within the pleural cavity. Such high negativity can be damaging to the pleural cavity and may also cause the liquid within the underwater seal chamber to be drawn up into the pleural cavity. In addition, even with a surgical drainage device having a separate underwater seal chamber, the entire seal can be lost during periods of high negativity in the pleural cavity. The loss of the water seal has the potential for serious damage in the event that the suction becomes disconnected. Thus, there is need for a means for providing instant relief for the condition of excess negativity in the pleural cavity.

SUMMARY OF THE INVENTION

The present invention provides a surgical underwater drainage device which overcomes the problems noted above with respect to prior art devices and provides an underwater drainage apparatus in which excess negativity can be relieved. Furthermore, the system provided assures that the excess negativity is relieved ony in small increments so that desired negativity is not lost.

According to the present invention, there is provided a surgical underwater drainage apparatus having a collection chamber with an underwater seal. Preferably, the underwater seal is located adjacent the lower end of the thorocotomy tube. Thus, when the thorocotomy tube is attached to the pleural cavity, liquid drained into the thorocotomy tube passes into the underwater seal chamber and forms the underwater seal. When the seal chamber is filled, the liquid overflows into the collection chamber.

There is further provided a metered air pump which is fluidly connected to the thorocotomy tube. This metered air pump is designed to deliver a metered volume of air to the thorocotomy tube during periods of excess negativity therein. During normal operation of the drainage device, the metered air pump does not permit the passage of any air into the thorocotomy tube. However, when excess negativity in the thorocotomy tube is discovered, the metered air pump is actuated to deliver a metered volume of air to the thorocotomy tube. The metered air pump is actuated as many times as necessary to relieve the excess negativity. Actuation of the metered air pump is stopped once the excess negativity is relieved so that the desired negativity is maintained in the thorocotomy tube and drainage device.

In a preferred embodiment of the present invention, the metered air pump includes a metered air chamber which is supplied with atmospheric air through a one-way valve. During actuation of the metered air pump, this one-way valve is closed and the air in the metered air chamber is forced past a resiliently biased closed one-way valve and into the thorocotomy tube. By use of these two one-way valves, atmospheric air is admitted to the thorocotomy tube only in metered volumes.

Additional features and advantages of the present invention will be apparent from a consideration of the following detailed description of the preferred embodiment of the invention in connection with the accompanying drawings.

BRIEF DESCRIPTION OF THE DRAWINGS

FIG. 4 is a cross sectional elevation view of the metered air pump depicted in FIG. 1 returning to the unactuated position of the metered air pump depicted in FIG. 1.

FIG. 5 is a partial perspective view of a surgical underwater drainage device.

DETAILED DESCRIPTION OF THE PREFERRED EMBODIMENT

Figure 1:
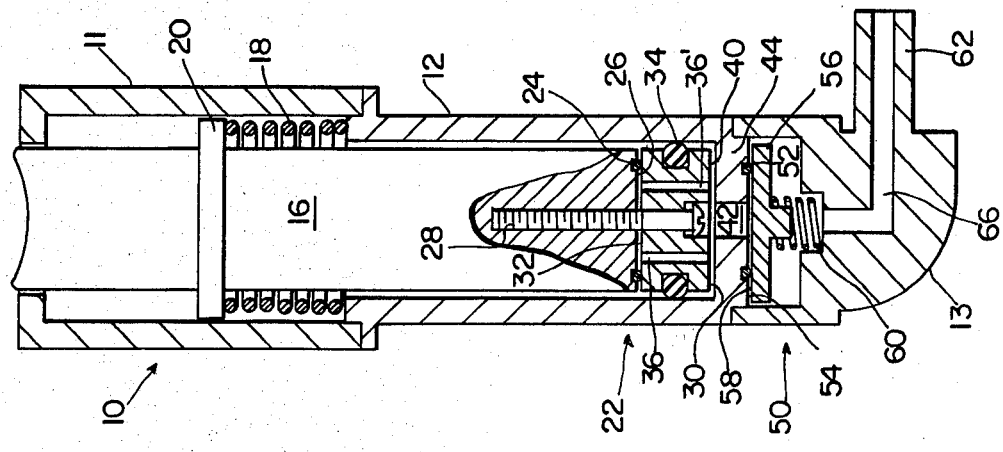
FIG. 1 is a cross sectional elevation view of the metered air pump of the present invention.

With reference now to the drawings in which like numerals represent like elements throughout the several views, a presently preferred embodiment of a metered air pump 10 is depicted in various stages of operation in FIGS. 1 to 4. As shown, metered air pump 10 has an upper housing 11, an intermediate housing 12, and a lower housing 13. Upper housing 11, intermediate housing 12, and lower housing 13 are suitably attached to one another to form a rigid structure. In the unactuated condition, a movable plunger 16 is located in upper housing 11. The plunger 16 extends beyond upper housing 11 at one end and into intermediate housing 12 at the other end. A spring 18 is located around plunger 12 between intermediate housing 12 and a stop 20 integral with plunger 16. Spring 18 presses against the top of intermediate housing 12 and stop 20 to urge stop 20 into contact with the top of upper housing 11 so that a portion of plunger 16 extends beyond upper housing 11.

Located at the lower end of movable plunger 16 is a one-way valve means 22. One-way valve means 22 includes an o-ring 24 located in the bottom face 26 of plunger 16. A screw 28 is threadably received in plunger 16. Slidably mounted on screw 28 is a piston 30 having a top face 32. The head on screw 28 engages piston 30 to prevent more than a slight separation between bottom face 26 under plunger 16 and top face 32 of piston 30. Carried around piston 30 so as to engage the sides of intermediate housing 12 is a piston seal 34. Extending through piston 30 are two open channels 36 and 36'.

As shown best in FIG. 1, a metered air chamber 40 is located in intermediate housing 12 below piston 30. An outlet 42 for metered air chamber 40 is provided in the bottom wall 44 of intermediate housing 12. Provided below bottom wall 44 is a normally closed one-way valve means 50. One-way valve means 50 includes an o-ring 52 located in the bottom face 54 of bottom wall 44. A cross wall 56 having a top face 58 is resiliently urged against o-ring 52 by a spring 60. Lower housing 13 is provided with a hose coupling 62 to which a hose 64 is attached. A passageway 66 provides fluid communication through lower housing 13 from outlet 42 to hose 64.

Depicted in FIG. 5 is a portion of a surgical underwater drainage device 70. Drainage device 70 has a collection chamber 72 having an underwater seal means 74. In the type of drainage device 70 depicted, underwater seal means 74 has an underwater seal which is formed by liquid 76 which is drained from the patient's pleural cavity. Collection chamber 72 includes therein a portion of an inlet duct 78 which is adapted to be fluidly connected to the patient through a thorocotomy tube 80. The lower floor of collection chamber 72 includes a recesses "cup" portion 82 into which inlet duct 70 opens. Collection chamber 72 is connected to a suitable source of negative pressure so that fluids in the pleural cavity of the patient are drawn into collection chamber 72. A more complete description of the operation of similar drainage devices is contained in applicant's pending U.S. application Ser. Nos. 107,329 now U.S. Pat. No. 4,312,351, issued Jan. 26, 1982 and 120,295 now U.S. Pat. No. 4,324,244, issued Apr. 13, 1982 which disclosures are herein incorporated by reference.

Inlet duct 78 extends through drainage device 70 and suitable hose 84 is connected thereto. In order to fluidly connect hose 64 with thorocotomy tube 80, a connection 86 is inserted in hose 84, hose 64 and thorocotomy tube 80.

In operation, surgical underwater drainage device 70 operates with metered air pump 10 fluidly connected to thorocotomy tube 80 in the following manner. During normal operation of the drainage device 70, liquids drained from the patient through thorocotomy tube 80 enter collection chamber 72 through inlet duct 78 and are collected in cup portion 82. As soon as enough liquid is collected in cup portion 82 up to the level of the opening of inlet duct 78, an underwater seal is formed. As shown in FIG. 5, enough liquid 76 has been collected in collection chamber 72 so that collection chamber 72 is almost filled halfway. With the desired degree of suction in chamber 72, the height of collected liquid in inlet duct 78 is approximately at the level 86 shown.

During periods of excess negativity, such as occurs during a blockage in the bronchial tubes of the patient, the liquid level in inlet duct 78 rises to a level such as shown by level 88. So long as the liquid level in inlet tube 78 remains at level 88, an excess negativity will exist in thorocotomy tube 80 and in the pleural cavity of the patient. In order to relieve this excess negativity, metered air pump 10 is actuated one or more times to pump a volume of air into thorocotomy tube 80 which is sufficient to relieve the excess negativity.

The operation of metered air pump 10 is as follows. Metered air pump 10 is shown in the unactuated, rest position, in FIG. 1. While at rest, metered air chamber 40 is in fluid communication with the surrounding atmospheric air by a passage which leads through ooen channel 36 and 36', around plunger 16 and stop 20 of plunger 16, and through the opening in upper housing 11 through which plunger 16 extends. This open fluid communication assures that atmospheric air is present in metered air chamber 40 prior to actuation of metered air pump 10. It should also be noted that while metered air pump 10 is in the rest position, metered air chamber 40 is not in fluid communication with thorocotomy tube 80 due to the action of normally closed one-way valve means 50. Consequently, atmospheric air from metered air chamber 40 is only conducted to thorocotomy tube 80 upon actuation of metered air pump 10.

Figure 2:
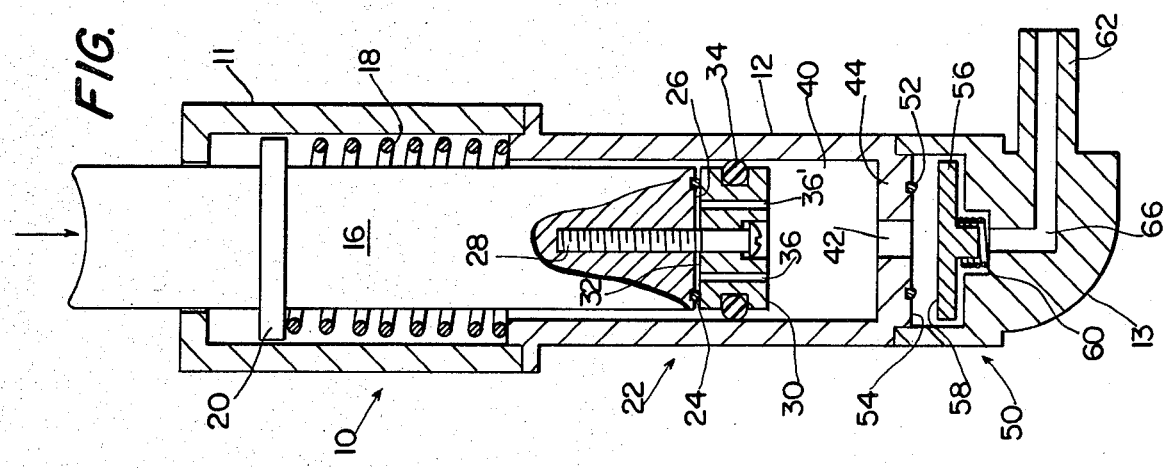
FIG. 2 is a cross sectional elevation view of the metered air pump depicted in FIG. 1 during actuation of the metered air pump.

After excess negativity has been noted in surgical underwater drainage device 70, as by the rising of the liquid 76 to liquid level 88, metered air pump 10 is actuated. Actuation of metered air pump 10 is produced by depressing the portion of plunger 16 which extends above upper housing 11. In FIG. 2, plunger 16 is being depressed. As shown, as soon as plunger 16 is depressed, bottom face 26 of plunger 16 travels towards top face 32 of piston 30 as screw 28 slides relative to piston 30. After a short distance, o-ring 24 located in bottom face 26 engages top face 32 and forms a seal. This seal cuts off fluid communication between metered air chamber 40 and the surrounding atmosphere so that the air in metered air chamber 40 is trapped. Further depression of plunger 16 causes pressure to build up in metered air chamber 40 which is sufficient to cause cross wall 56 to move downward against the force of spring 60. As soon as cross wall 56 moves, the air trapped in metered air chamber 40 passes through outlet 42, around cross wall 56, and through passageway 66 and hose 64 to thorocotomy tube 80.

Figure 3:
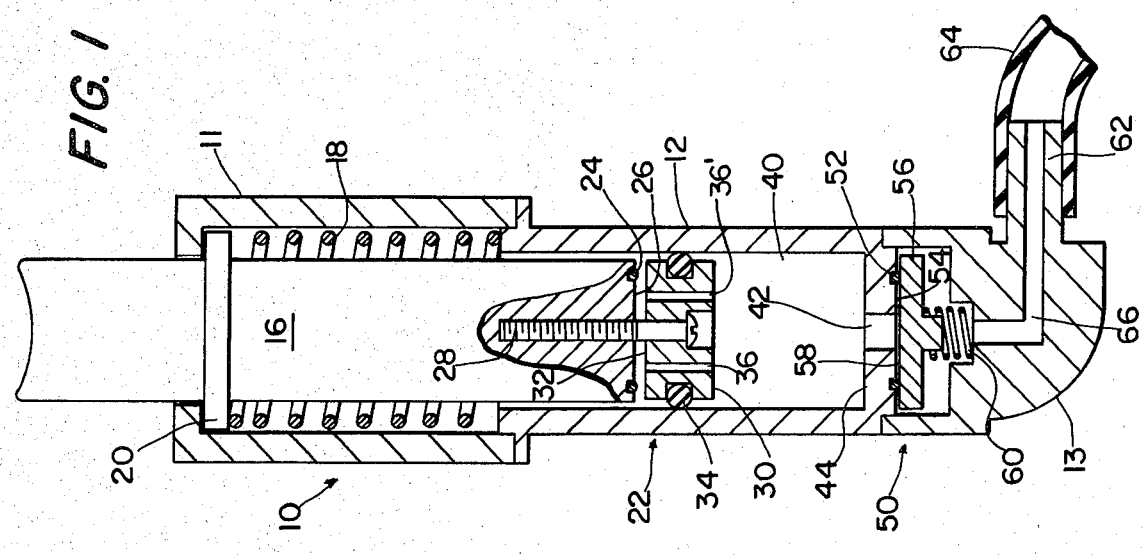
FIG. 3 is a cross sectional elevation view of the metered air pump depicted in FIG. 1 after actuation of the metered air pump.

The full depression of plunger 16 is depicted in FIG. 3. After full depression of plunger 16, the volume of air which was contained in metered air chamber 40 has been delivered to thorocotomy tube 80 to relieve the excess negativity therein. As there is no longer any air pressure in metered air chamber 40, top face 58 of cross wall 56 is returned to sealing engagement with o-ring 52 by the force of spring 60. Thus, there is no longer any fluid communication between metered air chamber 40 and thorocotomy tube 80.

After delivery of the air from metered air chamber 40, plunger 16 is released and travels upward in upper housing 11 due to the action of spring 18. As shown in FIG. 4, immediately after release of plunger 16, top face 32 of piston 30 is separated from o-ring 24 carried in bottom face 26 of plunger 16. Bottom face 26 continues to separate from top face 32 until the head of screw 28 engages piston 30 as piston 30 slides along screw 38. Thus, fluid communication between metered air chamber 40 and the surrounding air is immediately provided upon release of plunger 16. In this manner, during the travel of plunger 16 back to its initial position with stop 20 resting against the top of upper housing 11, atmospheric air is drawn into metered air chamber 40' around plunger 16 and through open channels 36 and 36'. It should be appreciated that the flow of atmospheric air into metered air chamber 40 is caused by the negative pressure produced in metered air chamber 40 as piston 30 moves upward in intermediate housing 12 away from normally closed one-way valve means 50. As soon as stop 20 reaches the top of upper housing 11, metered air pump 10 has returned to its initial position as depicted in FIG. 1 and is again ready to deliver a metered volume of air from metered air chamber 40 to thorocotomy tube 80 as necessary.

In summary, metered air pump 10 provides a means for delivering a small volume of air to thorocotomy tube 80 to releave excess negativity therein. Because metered air pump 10 is not open to the atmosphere during delivery of the metered volume of air, only the metered volume of air is received in thorocotomy tube 80. By designing metered air chamber 10 to have a small volume, the volume of air delivered to thorocotomy tube 80 is only large enough to reduce the excess negativity therein and does not destroy the desired negativity.

Although the invention has been described relative to an exemplary embodiment thereof, it will be understood that variations and modifications can be effected in this embodiment without departing from the scope and spirit of the invention.

We claim:

1. A metered air pump for relieving excess negativity in an inlet tube of a surgical underwater drainage device comprising:
    a surgical underwater drainage device having an inlet tube;
    an elongate hollow body having an upper end and a lower hose fitting;
    an elongate plunger means mounted for reciprocal movement in said body, said plunger means being resiliently urged toward the upper end of said body so that in a rest position a portion of said plunger means extends beyond the upper end of said body;
    a metered air chamber located in said body below said plunger means;
    a pump air inlet which provides fluid communication between the open atmosphere and said metered air chamber;
    a pump air outlet at the bottom of said body which provides fluid communication between said metered air chamber and said lower hose fitting;
    means to seal said pump air inlet fluidly from said metered air chamber when said plunger means is depressed;
    means to seal said pump air outlet fluidly from said metered air chamber when said plunger means is undepressed; and
    means to connect said hose fitting fluidly with the inlet tube;
    such that when excess negativity is present in the inlet tube, said plunger means causes a metered amount of air to be injected into the inlet tube to relieve the excess negativity.

2. A metered air pump as claimed in claim 1 wherein said means to seal said pump air inlet is a normally open one way valve which closes in response to a positive pressure produced in said metered air chamber as said plunger means is depressed.

3. A metered air pump as claimed in claim 2 wherein said normally open one-way valve includes a piston with a peripheral seal engaging said elongate hollow body, said piston being operably connected to said plunger means between said plunger means and said metered air chamber so as to be movable relative to said plunger means; at least one open channel through said piston between said plunger means and said air chamber; and a piston seal located between said piston and said plunger means and peripherally to said at least one open channel so as to engage mating surfaces of said piston and said plunger means when said plunger means is depressed and to thereby prevent fluid communication between said pump air inlet and said at least one open channel.

4. A metered air pump as claimed in claim 3 wherein said piston is operably connected to said plunger means by a screw having a screw head, said screw being slidably mounted through said piston and threadably received in said plunger means.

5. A metered air pump as claimed in claims 1 or 2 wherein said means to seal said pump air outlet includes a resiliently biased closed one-way valve which opens in response to a positive pressure produced in said metered air chamber as said plunger means is depressed.

6. A metered air pump as claimed in claim 5 wherein said resiliently biased closed one-way valve includes a cross wall located in the bottom portion of said elongate body; an aperture in said cross wall; a spring biased closure urged toward said cross wall; and a seal located between said cross wall and said closure and peripherally to said aperture so as to engage mating surfaces of said cross wall and said closure when said plunger means is not depressed to thereby prevent the passing of air from said metered air chamber to said inlet tube.

7. A surgical underwater drainage apparatus for draining fluids from the body of a patient comprising:
    a container;
    a fluid inlet duct in said container;
    a collection chamber formed in said container for collecting fluids received through said fluid inlet duct, said collection chamber being fluidly connected to a suction source;
    an inlet tube fluidly connected at one end to the patient and at the other end to said fluid inlet duct;

an underwater seal located in said container for preventing the flow of the atmospheric air from said container into said inlet tube; and a metered air pump means for delivering a metered amount of air to said inlet tube when excess negativity occurs in said inlet tube, said metered air pump means including a metered air chamber means from which only a metered volume of air is pumped into said inlet tube upon actuation of said metered air pump means to control the vacuum level in the container.

8. A surgical drainage apparatus as claimed in claim 7 wherein said metered air pump means further includes a normally open one-way inlet valve which admits air to said metered air chamber means, said normally open one-way valve closing in response to actuation of said metered air pump means which causes a positive pressure in said metered air chamber means.

9. A surgical drainage apparatus as claimed in claim 8 wherein said metered air pump means further includes a resiliently biased closed one-way valve located between said metered air chamber means and said inlet tube, said resiliently biased closed one-way valve opening to pass air contained in said metered air chamber means to said inlet tube in response to the positive pressure produced in said metered air chamber means during actuation of said metered air pump.

10. A surgical drainage apparatus as claimed in claim 9 wherein said metered air pump means further includes a spring biased plunger located adjacent said metered air chamber means, said plunger being depressed to produce a positive pressure in said metered air chamber means which causes the air in said metered air chamber means to pass through said resiliently biased closed one-way valve and into said inlet tube.

11. A surgical drainage apparatus as claimed in claims 7 or 9 wherein said underwater seal is formed at the lower end of said fluid inlet duct, the fluids from the body of the patient forming the liquid in the underwater seal.

12. A surgical drainage apparatus as claimed in claim 7 wherein said metered air pump means comprises an elongate hollow body having an upper end and a lower hose fitting, an elongate plunger mounted for reciprocal movement in said body, said plunger being resiliently urged toward the upper end of said body so that in a rest position a portion of said plunger extends beyond the upper end of said body, said metered air chamber means located in said body below said plunger, a pump air inlet means to provide fluid communication between the open atmosphere and said metered air chamber means, a pump air outlet at the bottom of said body which provides fluid communication between said metered air chamber means and said lower hose fitting, means to seal said pump air inlet fluidly from said metered air chamber means when said plunger is depressed, and means to seal said pump air outlet fluidly from said metered air chamber means when said plunger is undepressed.

* * * * *